United States Patent [19]

Moll et al.

[11] Patent Number: 4,747,358
[45] Date of Patent: May 31, 1988

[54] SURGICAL SUTURING MACHINE

[75] Inventors: Philip Moll, Aachen; Georg Schlondorff, Roetgen, both of Fed. Rep. of Germany

[73] Assignee: G.M.Pfaff Aktiengesellschaft, Fed. Rep. of Germany

[21] Appl. No.: 9,197

[22] Filed: Jan. 29, 1987

[30] Foreign Application Priority Data

Jan. 30, 1986 [DE] Fed. Rep. of Germany ....... 3602725
Jan. 12, 1987 [DE] Fed. Rep. of Germany ....... 3700639

[51] Int. Cl.⁴ .......................... D05B 1/00; D05B 1/24; D05B 27/10
[52] U.S. Cl. .................................... 112/169; 112/197; 112/177; 112/322
[58] Field of Search ............... 112/169, 162, 176, 177, 112/322, 197, 199

[56] References Cited

U.S. PATENT DOCUMENTS

| | | | |
|---|---|---|---|
| 2,193,180 | 3/1940 | Mann | 112/177 |
| 2,751,870 | 6/1956 | Buono | 112/177 X |
| 4,027,608 | 6/1977 | Arbuckle | 112/169 |
| 4,258,639 | 3/1981 | Bonalumi | 112/322 |
| 4,487,143 | 12/1984 | Hiltner | 112/169 X |
| 4,553,544 | 11/1985 | Nomoto et al. | 112/169 X |

FOREIGN PATENT DOCUMENTS 2050448  1/1981  United Kingdom ............... 112/169

Primary Examiner—H. Hampton Hunter
Attorney, Agent, or Firm—McGlew and Tuttle

[57] ABSTRACT

The surgical suturing machine comprises a housing (10) on whose head piece (14) a needle holder (16) holding a needle (30), a thread catcher (18), a rotatable cylindrical body (20), a fixed foot with a plate (70) and a stretcher (22) are releasably mounted. The projecting tissue edges to be sutured together are clamped between plates (70) and cylindrical body (20). When the surgical suturing machine advances, the shaped circumferential surface (78) of cylindrical body (20) rolls along the outside of one edge of the tissue. The circumferential surface (78) of the rotating cylindrical body "grips" the outer surface of one tissue edge and guides the two tissue edges into a clamping zone which is located in the vicinity of the shortest distance between plate (70) and circumference (78) of the cylindrical body (20). The projecting tissue edges are pierced by needle (30) in the clamping zone and sutured together with the aid of thread catcher (18) and needle (30). Then they are pressed flat by stretcher (22) so that the edges of the tissue are opposite and abutting one another.

In a second embodiment a suction air holding device (240) which acts during each suturing process is provided in the suturing area of needle (203) for the tissue edges, said device (240) being raisable and lowerable by drive mechanism (236–239) in the vertical plane.

17 Claims, 7 Drawing Sheets

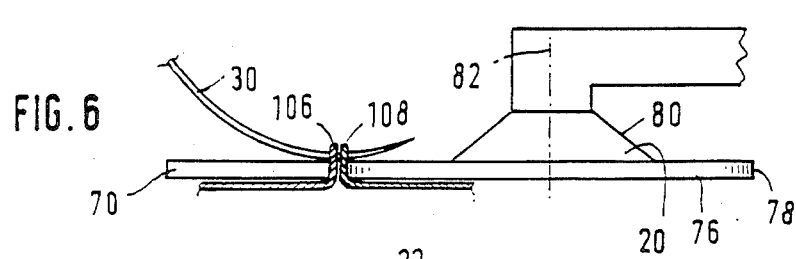
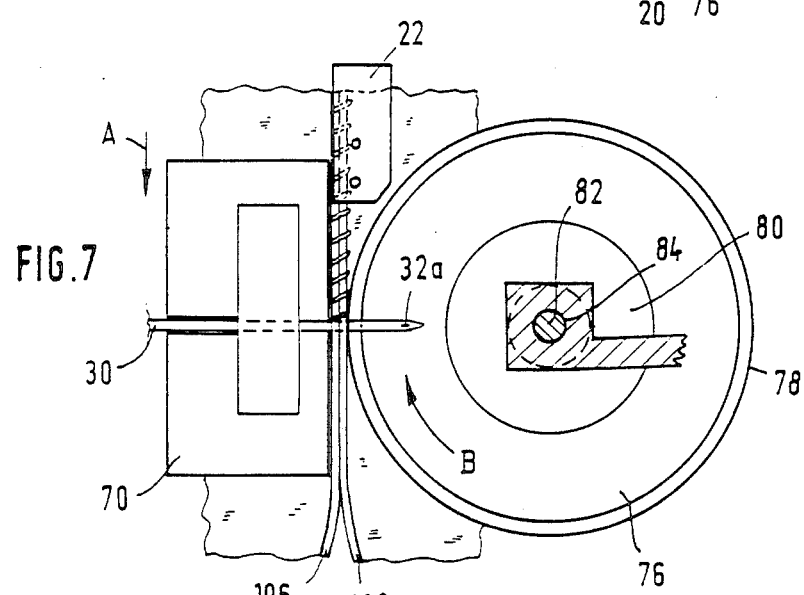
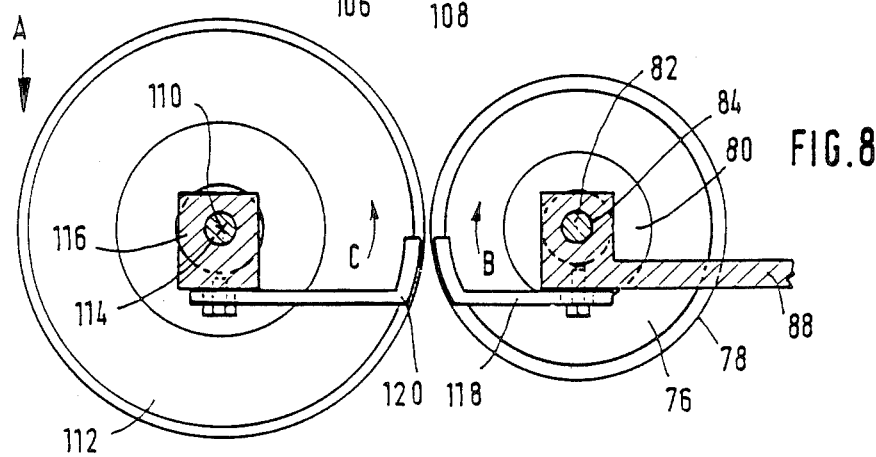
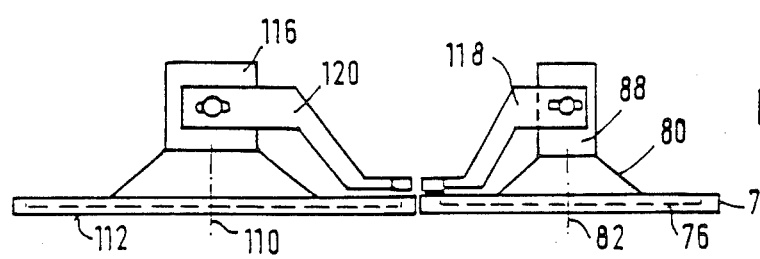

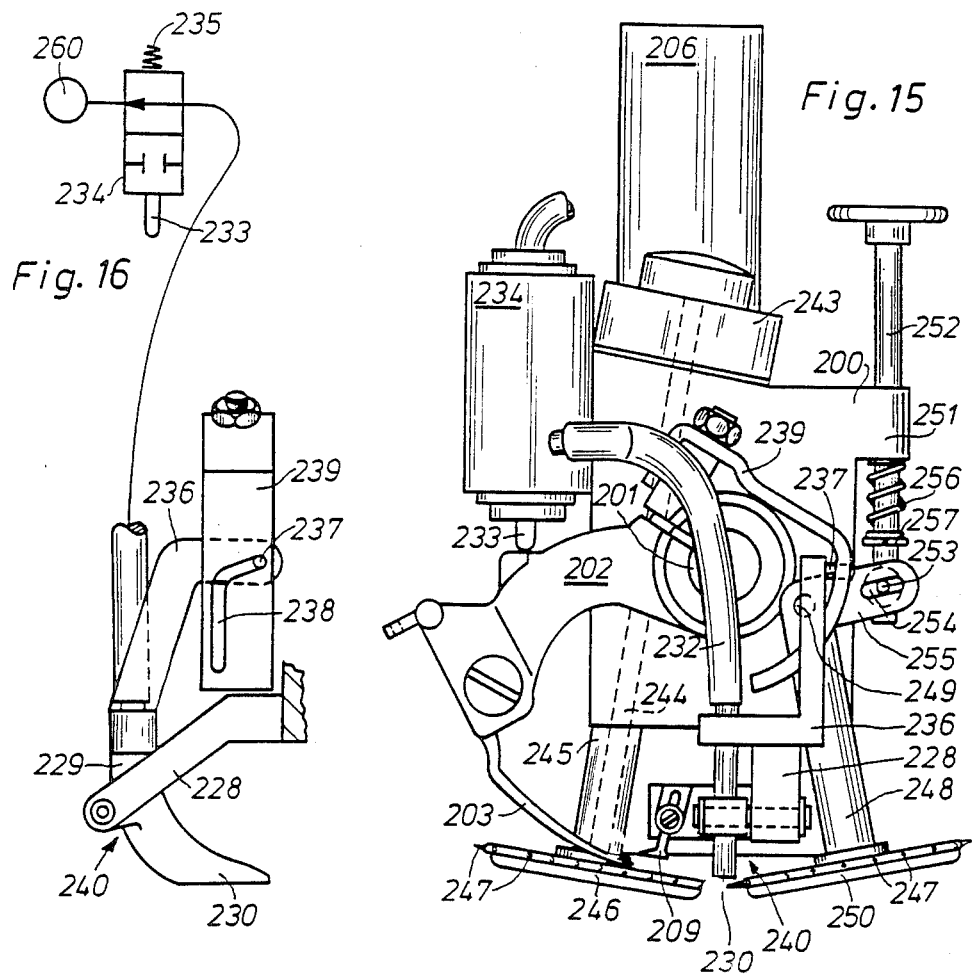
Fig. 15
Fig. 16
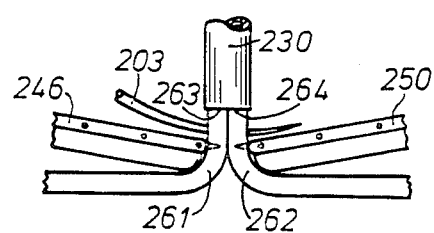
Fig. 17

SURGICAL SUTURING MACHINE

FIELD AND BACKGROUND OF THE INVENTION

This invention relates to a surgical suturing machine with a needle connected to a suture thread and driven in an oscillating manner, said needle cooperating with a thread catcher, and with two clamping elements, between which the edges of the tissue to be sewn are clamped and whose clamping zone is traversed by the needle transversely to the path of the suture.

A surgical suturing machine of this type is described in German OS No. 30 18 892. It comprises an oscillating needle through whose eye a suture thread is pulled. To sew tissue edges together, the latter are clamped between two clamping elements and held in this fashion. The two clamping parts are designed as straight rails connected together at one end by a hinge and held together by means of an arterial clamp or the like when the tissue edges are held together at the other end. The tissue edges are then rotated and aligned with their inner sides abutting one another between the two clamping elements which have their edges facing the surface of the body, i.e. in the clamping zone. The clamping elements comprise lengthwise slots which overlap one another and run parallel to the clamping zone, through which slots the needle passes to penetrate the tissue. The needle, driven in an oscillating fashion, then traverses the clamping zone transversely to the path of the suture. The needle cooperates with a thread catcher, producing the suture. When two tissue edges are sewn together, the latter must first be clamped between the clamping elements. To produce the suture, the part of the surgical suturing machine with the needle and the thread catcher must be placed on the clamping elements. To make the suture, the part of the surgical suturing machine with the needle and the thread catcher must be advanced by hand on the clamping elements along the clamping zone after each passage of the needle through the tissue edges. This does not produce an overlapping suture; rather, there is only a series of individual passages of the needle through the aligned tissue edges and, when the suture is smoothed, a row of lock stitches is left on either side of the wound. In addition, no protection against damage to the thread is possible and the suture may open inadvertently. In addition, only sutures that run in a straight line can be produced, in other words, only tissue edges which run in a straight line can be sutured together. The length of a suture to be prepared is determined by the clamping elements or by the lengthwise slots in the clamping elements. To make sutures that are longer than the clamping elements, most of the surgical suturing machine must be removed from the clamping elements, the clamping elements loosened, and the tissueedges still to be sutured clamped between the clamping elements. This procedure is tedious and prolongs the operation.

SUMMARY AND OBJECT OF THE INVENTION

It is an object of the invention to provide a surgical suturing machine by means of which the tissue edges, regardless of their shape and length, can be sutured together continuously and without interruption.

This object is achieved according to the invention by virtue of the fact that at least one clamping element is a rotatable cylindrical body whose circumference rolls along the outer surface of one tissue edge. The surgical suturing machine according to the invention comprises at least one clamping element designed as a rotatable cylindrical body. The other clamping element can be fixed. The tissue edges to be sutured are clamped between these two clamping elements so that they project and partially abut one another. As the surgical suturing machine advances along the suture, the cylindrical body rotates, with its circumferential surface rolling on the outer surface of one tissue edge, while the outer surface of the other tissue edge moves past the opposite, fixed clamping element. The upper edges of the projecting, clamped tissue edges are exposed between these travelling clamping elements, so that any kind of overlapping sutures can be produced which have proven especially advantageous in surgery because they are durable and yet easily removed.

In the surgical suturing machine according to the invention, the tissue edges to be sutured do not have to be clamped over their entire length between the clamping elements before suturing. At all times, only the part of the tissue edges which is about to be sutured is clamped. As the surgical suturing machine advances, the circumference of the rotating cylindrical body presses against the outer surface of one projecting tissue edge, whose inner surface is thus pressed against the inner surface of the other outwardly supported tissue edge. In the area of the shortest distance between the circumference of the cylindrical body and the other clamping element the two tissue edges are held clamped together. In other words, clamping takes place as the surgical suturing machine advances continuously and automatically, so that sutures of any length can be made without interruption. It is also possible to suture tissue edges running in any direction. The tissue edges to be sutured can lie on a curved line, e.g. they can be s-shaped. As the result of there being at least one rotatable cylindrical body, the path of the tissue edges can readily be followed by advancing the surgical suturing machine accordingly.

The suture produced with the aid of a surgical suturing machine is produced in a single suturing process without interruption, in other words, without shifting the surgical suturing machine. The tissue edges are sutured together with an overlapping suture securely and quickly by machine, shortening the length of the operation. The rotatably cylindrical body is driven either by the advance of the suturing machine, in which case the circumference of the cylindrical body rolls on the outer surface of one tissue edge and the cylindrical body is moved in a rotary fashion. Another possibility is to provide a separate drive for at least one cylindrical body.

According to one advantageous embodiment of the invention provision is made such that the upper end of the cylindrical body is suspended by a rotary means with an adjusting device for disengaging or engaging the cylindrical body with respect to the second clamping element, and by the fact that the lower end of the cylindrical body forms an essentially free sliding surface. With the aid of the adjusting device the cylindrical body can be disengaged from the second clamping element in order to bring the projecting tissue edges between the clamping elements when the suturing process begins. Then the cylindrical body is moved against the second clamping element with the aid of the adjusting device and the tissue edges are clamped. The lower end of the cylindrical body can be a smooth surface. This lower end contacts the patient's skin during the suturing process, i.e. the area of the skin which abuts the tissue edge on whose outer surface the circumference of the rotatable cylindrical body is rolling. The adjusting device as well as the lower end of the cylindrical body which is free from machine components provides simple handling of the surgical suturing machine both during "tensioning" of the tissue edges at the beginning of the suturing process and also as the suturing machine is advanced.

Advantageously, provision is made such that the adjusting device comprises a spring-elastic adjustable device for changing the clamping force of the cylindrical body. In this way the clamping force of the cylindrical body against the second clamping element can be adjusted. The clamping force can thus be adjusted to suit tissue edges of different thicknesses.

One advantageous embodiment of the invention is characterized by the fact that the cylindrical body is depressed in the clamping zone on the feed side of the tissue and by the fact that the circumference of the cylindrical body is shaped to form a drive ring. Tilting the axis of rotation in turn tilts the part of the cylindrical body pointing in the direction of motion of the surgical suturing machine downward, while the part of the cylindrical body which is diametrally opposite this part is elevated accordingly. The position of the cylindrical body relative to the needle is then such that the needle can move freely beyond the upper end of the cylindrical body after passing through the edges of the tissue. The circumference of the cylindrical body is shaped so that engagement of the tissue edge on whose outer surface the circumference rolls, is improved. In addition, projecting and backward pointing pins or suction cups can be provided on the circumference. As the surgical suturing machine advances, the tissue edge is "caught" by the circumference of the cylindrical body, designed as a drive ring, in the part which points in the feed direction of the surgical suturing machine, and is lifted along with the projecting tissue edge abutting the second clamping element so that the tissue edges project above the clamping elements in the suturing area of the needle, in other words, in the clamping zone of the clamping elements. The sloping position of the cylindrical body as well as the special design of its circumference thus produces a reliable feed of the tissue into the clamping zone. In one advantageous embodiment of the invention, provision is made such that the cylindrical body is a circular disk. As a result the surgical suturing machine can be made compact and with small dimensions. A roller, a roll, or a strip can also be used instead of a circular disk.

In another embodiment of the invention a needle guide surface and/or a fixed needle guide are disposed at the upper end of the cylindrical body. During the suturing process the needle, after passing through the tissue edges, moves beyond the upper end of the cylindrical body. In order to protect the needle against deflection transversely to its direction of oscillation, the upper end of the cylindrical body can be designed as a needle guide surface to guide the needle. Another possibility consists in the fact that a needle guide is disposed above the upper end, said guide preventing deflection of the needle. The needle guide is fixed and so disposed that the cylindrical body rotates beneath it. These two measures ensure that the motion of the needle is stabilized. This in turn means that the holes made in the tissue edges are not dilated because deflection of the oscillation direction of the needle after penetrating the tissue edges is prevented.

In another advantageous embodiment of the invention, provision is made such that a fixed support device for excess tissue is disposed on the upper end of the cylindrical body of the vicinity of the clamping zone. The supporting device prevents the excess tissue (the part of the tissue edge which projects above the clamping elements) from being pressed down as the needle passes through. This ensures that the tissue edges are pierced by the needle at the same height and a uniform, perfect, durable suture is produced. The support device can be disposed on both clamping elements. A support device of this kind prevents the excess tissue from moving with the needle either when the needle is inserted or when it is withdrawn.

In another advantageous embodiment of the invention provision is made such that a stretcher for the suture is disposed on the exit side of the tissue from the clamping zone. The stretcher is disposed behind the needle relative to the motion of the surgical suturing machine and presses flat that portion of the suture which has just been formed. The stretcher pushes down the projecting tissue edges which abut one another and have been sutured together so that their edges abut one another. The tissue edges can then grow together in this condition.

Advantageously, the stretcher comprises an elliptically movable presser foot. The latter is driven by an eccentric for example, and has an adjustable stroke. The presser foot slides over the suture and smooths it. It moves on an elliptical path such that it does not touch the suture when it moves in the forward direction of the suturing machine but presses down the suture when it moves opposite to the direction of motion of the surgical suturing machine. This ensures that the tissue edges are always pressed flat only when the presser foot is moving along with the suture. This results in an especially protective flattening of the part of the suture which has just been produced. As it flattens the suture, the stretcher or presser foot also advances the surgical suturing machine stepwise.

In another advantageous embodiment of the invention the thread catcher is designed as a forked arm which moves axially and on a path which is an arc of a circle and is driven in synchronization with the needle such that the thread catcher, after the needle has made a pass through the tissue, lifts the suture thread off the needle, places it above the clamping zone, and, before the next penetration of the needle through the tissue, locates it in front of the needle, in the clamping zone, in the direction of the feed side of the tissue. This cooperation between needle and thread catcher produces a single-thread suture in which the interface, in other words, the abutting tissue edges, is surrounded by a loop. After the needle has passed through the projecting tissue edges and pulled the suture thread with it, the direction of motion of the needle is reversed so that the needle moves backward; because of the friction between the suture thread and the tissue, the latter is twisted to form a loop. When the needle moves back again, the thread catcher moves on its axial path into the loop, lifting the thread off the needle. As the needle continues moving out of the tissue, the thread catcher describes a path which is an arc of a circle, guiding the loop over the edges of the tissue onto the suturing side of the tissue. As the thread catcher moves along its arcuate path, the suture moves away beneath the surgical suturing machine so that the needle does not penetrate the tissue at the same point. After the thread catcher has located the thread loop above the tissue edges and in the direction of the feed side of the tissue in the clamping zone ahead of the needle, the thread catcher moves back in the axial direction. The needle, which has moved toward the tissue edges, passes through the thread loop and into the tissue. This produces a single thread blind stitch-chain stitch suture which overlaps the interface, i.e. the tissue edges. However, it is also possible to make the blind stitch-chain stitch suture with two threads. The thread catcher will then cooperate accordingly with the second suture thread. The blind stitch-chain stitch suture makes it possible for the tissue edges which project and abut one another during the suturing process to be pressed flat by the stretcher after being sutured together so that the tissue edges are opposite and abut one another. In this condition the tissue edges can then grow together. In addition, the single thread blind stitch-chain stitch suture has the property that all of the suture material can be pulled out if the thread is separated at the correct point. This produces a suture especially simple to remove. If on the other hand the thread is separated not at this point but at another point, it is automatically protected against separation. Likewise, when completing a suture, the thread can be cut after completing one or more stitches at a predetermined point and then automatically knotted.

Another advantageous embodiment of the invention is characterized by the fact that drive and transmission elements for the cylindrical body, the needle holder, and the thread catcher are disposed in the housing of the surgical suturing machine, by the fact that the housing is provided with a gripper element, and by the fact that the cylindrical body, the needle holder, and the thread catcher are each releasably mounted by quick connections on the head side of the housing. The elements on the head part of the housing of the surgical suturing machine which must be sterilized can be releasably mounted rapidly and simply with the aid of the quick connections. This permits reliably rapid replacement of parts and facilitates sterilization of the surgical suturing machine.

The surgical suturing machine is powered by a conventional electric motor with needle height adjustment, so that single stitches as well as rows of stitches can be made. This motor also allows a thread cutter to be connected for separating the chain of stitches. This can also be done by hand with scissors.

To prevent the tissue edges gripped between the clamping elements and held laterally by the funnel-shaped narrowing of the support fingers from being squeezed, in an alternative embodiment of the invention at least one suction-air holding device for the tissue edges is provided, said device being effective during each suturing process, in the suturing area of the needle. The holding device operates by suction to hold the edges of the tissue edges to be joined during each stitching process so that the forces directed laterally and acting on the tissue edges during both the entry and exit of the needle as well as during retraction of the needle are taken up by the holding device; thus the clamping force of the clamping elements holding the tissue edges can be reduced and the support fingers can be eliminated completely. In this fashion pinching of the tissue is reliably avoided. A further reduction of clamping or compression force of the clamping elements can be accomplished when the clamping elements designed in the form of a wheel or wheels are provided on their circumferential surfaces with radially projecting needles, since in this case a positive driving connection exists between the clamping elements and the tissue edges.

According to another embodiment of the invention the holding device can be moved upward and downward in the vertical plane by a drive mechanism. This measure makes it possible to lift the segments of the tissue edges which are in the stitching area to the height which is required for reliable suturing with respect to the path of movement of the needle. By providing a suitable timing of the upward and downward movement of the holding device relative to the control of the suction which is effective only during the individual stitching processes for the holding device, a situation can be created in which the tissue edges in the holding device are separated in time from one another between two stitching proceses, in other words, during the time in which the needle is outside the tissue. In this fashion, after each stitching procedure, the advancing movement of the suturing machine relative to the fixed tissue can be accomplished smoothly. ;P According to another embodiment of the invention the drive mechanism of the holding device is drivably connected with the drive mechanism of the suturing machine and the stroke of the holding device is adjustable. The drivewise connection of the drive mechanism with the suturing machine drive mechanism, and preferably with the needle rod drive as well, not only derives the driving motion for the holding device from a transmission component of the suturing machine which is already in place, but also produces a synchronization of the motion of the holding device with the motion of the needle. Adjusting the stroke of the holding device makes it possible to change the distance of the penetration points of the needle from the cut edges of the tissue edges and thus the spacing of the stitches.

On the basis of another embodiment of the invention according to which the holding device has a suction foot extending flat opposite to the feed direction of the suturing machine, with a suction opening formed on the underside, the overlapping seam which joins the cut edges of the tissue can be partially formed by the suction foot so that the latter can be located directly in the suturing area. The sutures in this case are formed such that the needle first penetrates the lifted tissue edges below the suction foot and passes through them, pulling the suture thread with it. When the needle is retracted as a result of the friction of the suture thread in the tissue, a loop of thread is formed which the thread catcher receives, lifts over the cut edges and the suction tube, and places on the opposite side, ahead of the point where the needle will be inserted next. Before the needle is inserted again the suturing machine is advanced by an amount equal to the stitch length in the feed direction, whereupon the thread loop formed above the suction tube is pulled off.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 6 shows the projecting tissue edges clamped between the clamping elements, through which edges the needle is passing;

FIG. 7 is a top view of the clamping elements with projecting tissue edges clamped between them;

FIG. 8 is a top view of two rotatable cylinder bodies which function as clamping elements and are provided with a support device;

FIG. 9 is a front elevation of the two rotatable cylindrical bodies shown in FIG. 8;

FIG. 15 is a front elevation of a surgical suturing machine;

FIG. 16 is a view of the drive mechanism for the holding device;

FIG. 17 is a front elevation of a portion of the transport wheels and the needle during suturing.

DESCRIPTION OF THE PREFERRED EMBODIMENTS

Figure 1:
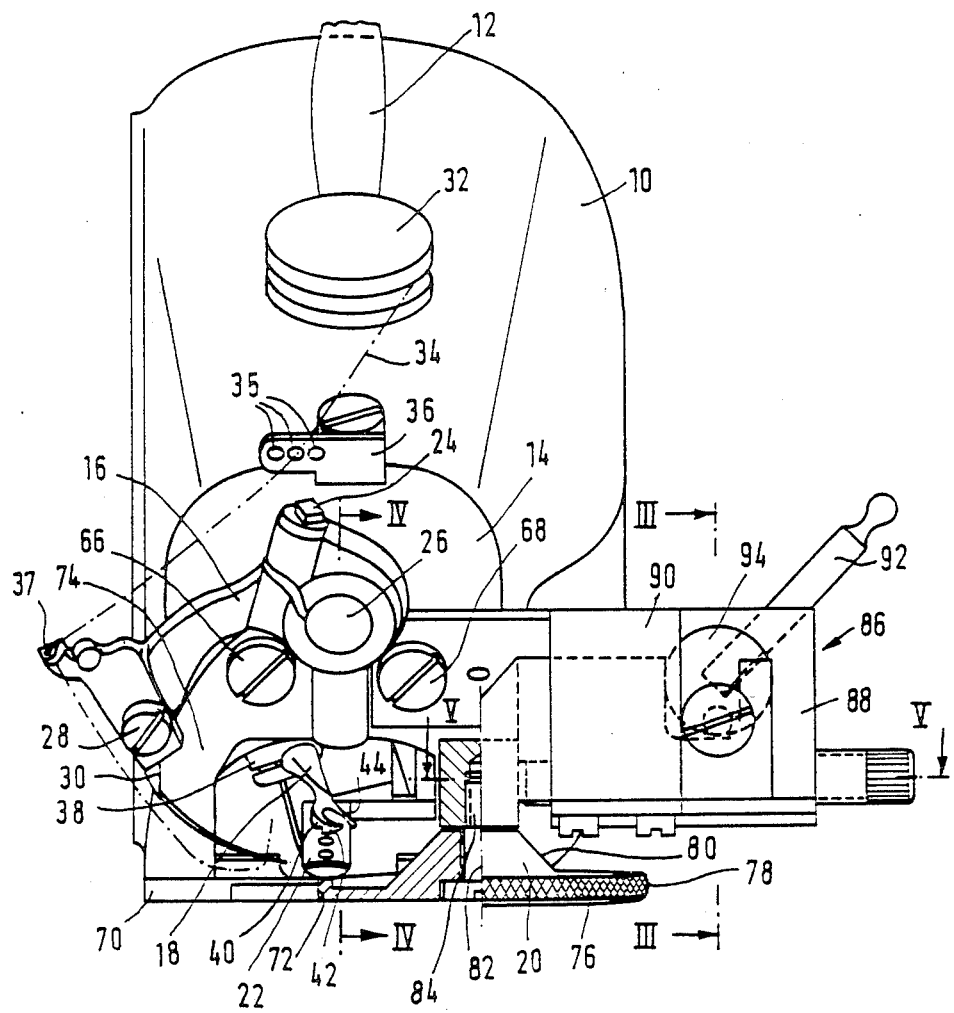
FIG. 1 is a front elevation of the surgical suturing machine.

FIG. 1 is a front elevation of the surgical suturing machine. It has a housing 10, on which a top handle 12 is disposed. On the left side of housing 10 is a removable housing cover (not shown). On the head side 14 of housing 10 of the surgical suturing machine, a needle holder 16, a thread catcher 18, and a circularly cylindrical disk-shaped body 20 are disposed. In addition, a stretcher 22 is located on the head side 14 of housing 10. Needle holder 16 has a clamp which is fastened by means of a screw 24 to an oscillating drive shaft 26 projecting from head piece 14. A suturing needle 30 is mounted on needle holder 16 by means of a screw 28. As shaft 26 oscillates, the point of the needle in which eye 32a is located describes a circular path. Suturing needle 30 is a round needle.

On the top of housing 10 a spool 32 is rotatably mounted in front of handle 12, on which spool suture thread 34 is wound. Thread 34 runs from spool 32 over a thread holder 36 through a hole in needle holder 16 to the pint of needle 30 where it is pulled through needle eye 32a. Thread holder 36 is designed as an angular element provided with at least one through hole, said element being tightly screwed to the edge of the top of housing 10 which abuts head piece 14. One leg of the angular element projects beyond head piece 14 and points upward. Through hole 37 of needle holder 16 is disposed at the end of needle holder 16 to which needle 30 is fastened. Thread catcher 18 is mounted to a clamping device 38 inside the housing and projects out of head side 14 of the surgical suturing machine below shaft 26. It is designed as an arm bent at an angle, whose forward free end is forked. One prong 40 of the forked end of thread catcher 18 is bent and has a hook 42 while the second prong 44 is merely straight. The motion and function of the thread catcher as well as those of the needle are described below.

Housing 10 of the surgical suturing machine contains the drive and transmission elements for needle holder 16, thread catcher 18, and stretcher 22. Shaft 26 is the transmission element for the pivoting motion of needle holder 16 and passes through a hole 46 in head piece 14 of housing 10. A sleeve 48 is mounted in hole 46, with shaft 26 mounted in said sleeve. Inside housing 10 is a projection 50 made integral with housing 10, said projection having a through hole 52 in which a sleeve 54 is fitted. Shaft 26 is mounted in sleeve 54 and runs from there to a drive (not shown) which rotates shaft 26 back and forth. This rotary motion of shaft 20 causes needle 30 held by needle holder 16 to oscillate.

Figure 2:
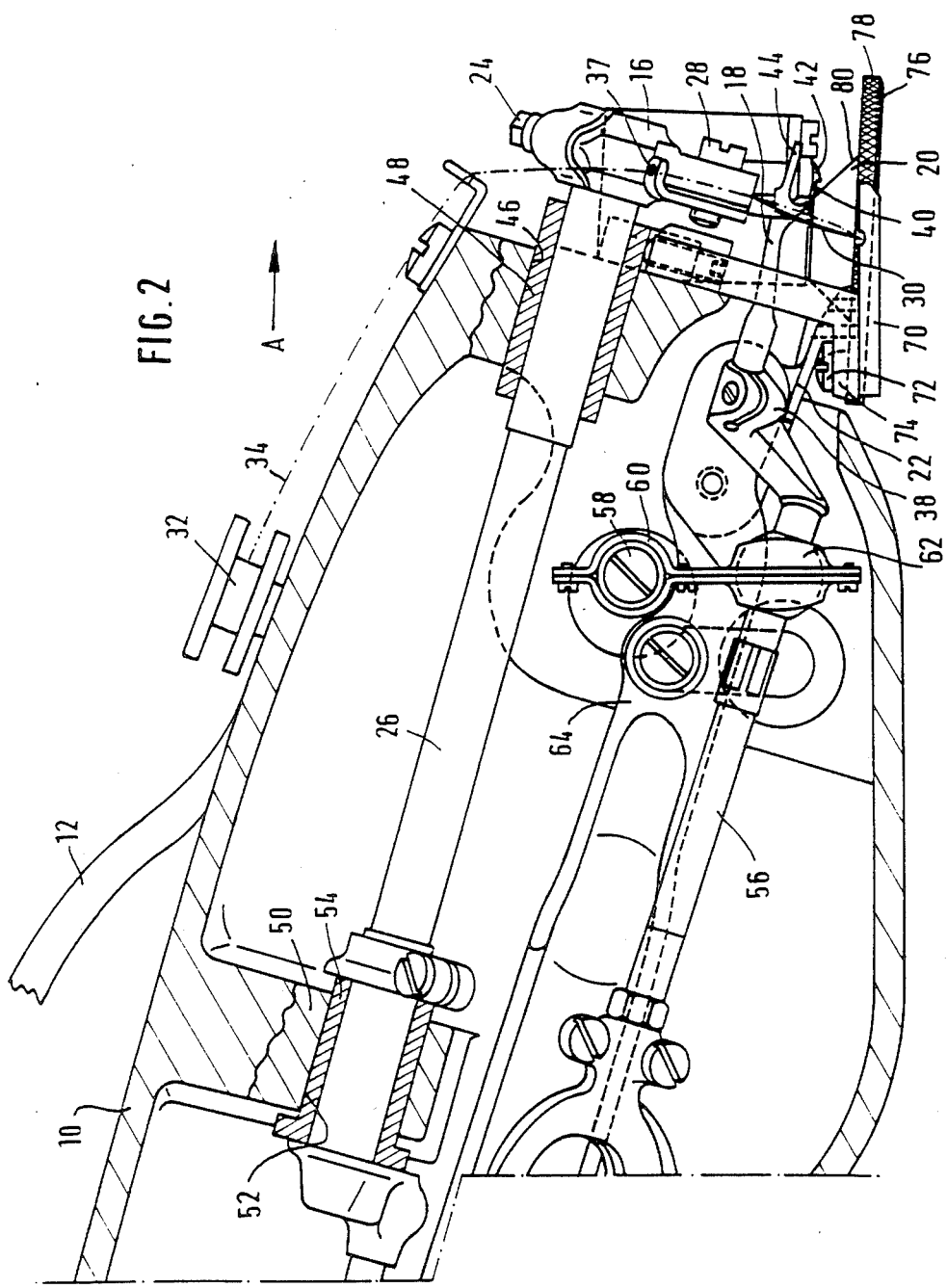
FIG. 2 is a side elevation of the surgical suturing machine according to FIG. 1 with the housing cover open.
Figure 3:
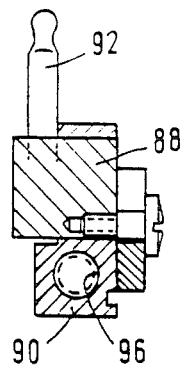
FIG. 3 is a section along line III—III in FIG. 1.

As already mentioned, thread catcher 18 is fastened to a clamping device 38 inside housing 10. Clamping device 38 is connected with a lever 56, which in turn is connected by a universal joint (not shown) with a drive shaft. Housing 10 contains a lever 60 rotatably mounted on a pin 58, with a ball bearing 62 disposed on the free end of said lever 60, said bearing 62 supporting lever 56. The rotary motion of the drive shaft is converted by the universal joint into a reciprocating motion of lever 56 whereupon a rotary motion about its lengthwise axis is superimposed on this motion of lever 56. During the motion of lever 56, the latter turns on ball bearing 62, with lever 60 pivoting about pin 58. In housing 10 of the surgical suturing machine there is a second lever 64 to whose forward end stretcher 22 is fastened and which projects out of head side 14 of housing 10. Lever 64 is connected with a drive shaft which moves it in such fashion that stretcher 22 describes an elliptical curve when the surgical suturing machine is viewed from the side (FIG. 2). The clamping elements of the surgical suturing machine, between which the projecting tissue edges are briefly clamped during suturing, are each fasened by a screw 66 or 68 to head piece 14 of housing 10. The first clamping element is designed as a fixed plate 70, along whose straight lengthwise edge 72 the outer surface of one tissue edge slides. Plate 70 is fastened by a screw 72 to one leg of an angular element 74, whose other leg is fastened to head piece 14 by means of screw 66. Plate 70 accordingly forms the immovable one of the two clamping elements.

The second element is designed as a rotatable cylindrical body 20, which in this embodiment of the surgical suturing machine is a disk 76. Disk 76 is so disposed relative to fixed plate 70 that its cylindrical circumferential surface or circumferential portion 78 faces the lengthwise edge of plate 70 on which the outer surface of one tissue edge slides. The underside of disk 76, which rests on the skin when the tissue edges are being sutured, is smooth. The upper end of disk 76 has a frustroconical elevation 80 at the center, which tapers upward. The upper end of elevation 80 is connected with a rotational axis 84 such that the latter is coaxial with central axis 82 of disk 76. Axis 84 is both rotatably and removably placed in a blind hole in an adjusting device 86, which is fastened by screw 68 to end 14 of housing 10. Adjusting device 86 consists of two mutually displaceable parts 89 and 90, with part 88 and disk 76, and part 90 with screw 68 being fastened to head side 14 of housing 10.

Figure 5:
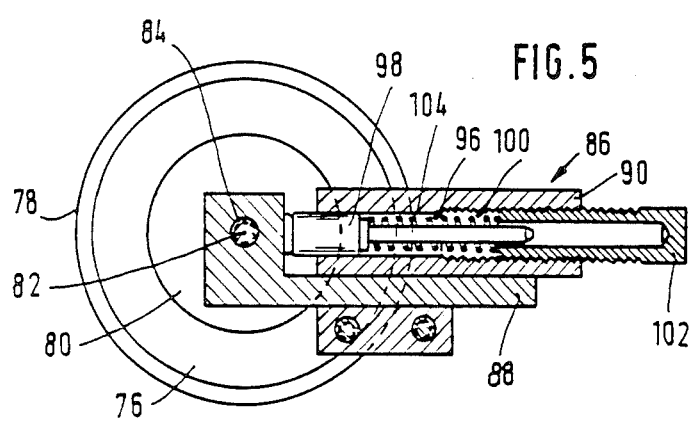
FIG. 5 is a section along line V—V in FIG. 1.

By means of a lever 92, pivotably mounted on part 90 of adjusting device 86, part 88 can be displaced relative to part 90 so that disk 76 moves toward plate 70 or away from it. Lever 92 is connected with an eccentric disk 94 which is rotatably mounted on part 90. The circumference of eccentric disk 94 contacts part 88, so that when lever 92 pivots, part 88 is displaced relative to part 90. A through hole 96 runs radially with respect to rotational axis 84 in disk 76 through part 90, the hole 96 having a piston 98 therein (FIG. 5). The end of hole 96 away from rotational shaft 84 is provided with an inside thread 100 which meshes with the outside thread of a screw 102. A coil spring 104 is located between piston 98 and screw 102, by means of which spring part 88 of adjusting device 86 is urged against plate 70 by piston 98. With the aid of screw 102 the force which coil spring 84 exerts on piston 98 and part 98 can be adjusted. When lever 92 pivots in the direction of housing 10 disk 76 moves away from plate 70 against the force of coil spring 104.

Figure 4:
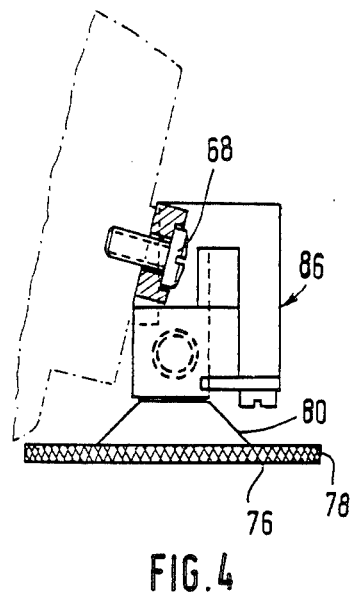
FIG. 4 is a section along line IV—IV in FIG. 1.

During suturing tissue edges 106 and 108 as shown in FIG. 6 are clamped so that they are upright and partially abut one another between plate 70 and disk 76. The outer surface of tissue edge 106 slides along the lengthwise edge of plate 70 facing disk 76, while the circumference 78 of disk 76 rolls along the outer surface of tissue edge 108. The free area of the tissue edges projecting above the lengthwise edge of plate 70 and disk 76 is penetrated by needle 30 and sutured with the suture thread. FIG. 7 shows the top view of the two tissue edges 106 and 108 to be sutured and shows how the two projecting tissue edges are "fed" into the clamping zone between the fixed foot with plate 70 and disk 76 as the surgical suturing machine moves in the direction of arrow A. As the suturing machine moves in the direction of arrow A, disk 76 rotates in the direction of arrow B. The circumferential surface 78 of disk 76, as shown in FIGS. 1, 2, and 4, is shaped as a rough grid of crossed lines. Circumferential surface 78 "hooks into" the outer surface of tissue edge 108 and pulls it along with tissue edge 106 into the clamping zone, in other words into the area where the distance between plate 70 and disk 76 is very small. Because of the tilted position of disk 76 shown in FIG. 2 relative to the fixed foot of the surgical suturing machine, tissue edge 108 together with tissue edge 106 is lifted as it is pulled into the clamping zone so that the tissue edges project sufficiently far above plate 70 and disk 76. Needle 30 passes through this projecting tissue as it sutures the two tissue edges together.

FIGS. 8 and 9 show a support device which supports the excess tissue against flopping over sideways as the tissue edges are sewn together. In this drawing also the fixed foot with plate 70 which functions as a fixed clamping element is represented by a flat disk 112 which is rotatable about rotational axis 110. The design of disk 112 corresponds to that of disk 76, with the diameter of disk 112 being greater than that of disk 76. In this case the two clamping elements are rotatable so that the circumferential surfaces of the two disks 76 and 112 each roll along an outer surface of the tissue edges. Rotational shaft 114 of disk 112 is held in a retaining device 116 which is mounted on head piece 14 of housing 10 of the surgical suturing machine. The support device for the excess tissue consists of two arms 118 and 120, with arm 118 displaceably mounted on part 88 of adjusting device 86 and arm 120 is displaceably mounted on holding device 116. Arms 118 and 120 are bent at an angle in the circumferential zones of disks 76 and 112 respectively, their free ends follow the arc of the disc for a short distance in the direction of the clamping zone and extend a slight distance above the disk in question. The two arms 118 and 120 are so disposed relative to disk 76 and 112 that their free ends, adapted to the circumference of the disk in question, in a top view have their edges aligned with the disks. As the surgical suturing machine moves in the direction of arrow A in FIG. 8, disk 76 rotates in direction B and disk 112 rotates in direction C beneath fixed arms 118 and 120. The tissue edges projecting above disks 76 and 112 and clamped between them are protected against flopping over sideways in the direction of disk 76 by arm 118 as needle 30 is inserted, while they are protected against flopping over sideways in the direction of disk 112 by arm 120 as the needle is withdrawn. The supporting device ensures that needle 30 penetrates the two raised tissue edges 106 and 108 at the same height as it sutures them producing a precise suture.

Figure 10:
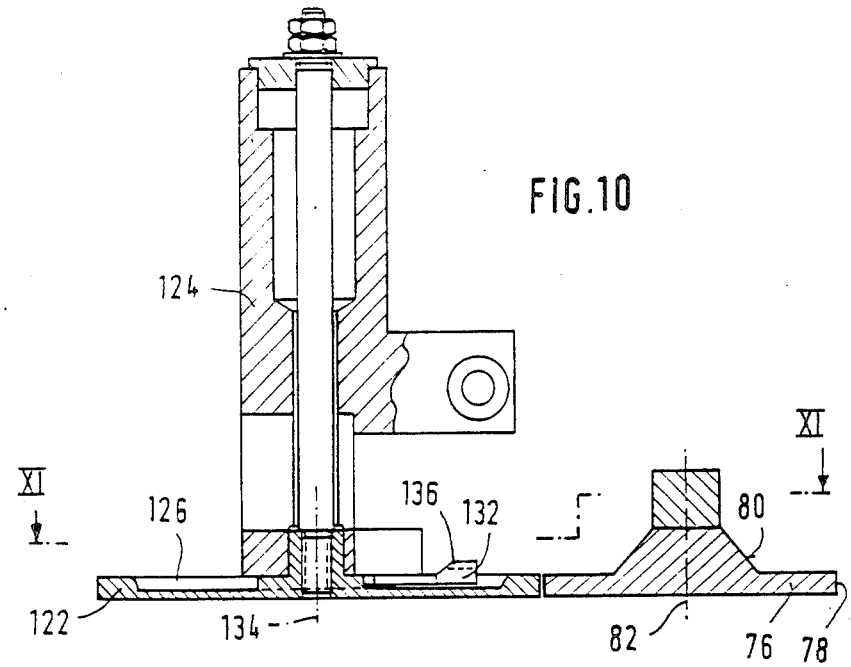
FIG. 10 is a cross section through rotatable cylindrical bodies functioning as clamping elements.

FIG. 10 shows another example of a rotatable disk 122 which can be used as a second clamping element instead of the fixed foot in the surgical suturing machine. Disk 122 is disposed at the level of disk 76 and its surface is rotatably mounted in a retaining device 124. Disk 122 has on its surface an annular depression 126. In depression 126, without contacting th surface of disk 122, there is a plate 128 permanently attached to retaining device 124. As disk 122 rotates the latter moves away beneath plate 128. Plate 128, at end 130 facing disk 76, has an elevation 132 pointing upward in which there is a groove which extends radially with respect to rotational axis 134 of disk 122 and radially with respect to rotational axis 82 of disk 76, said groove functioning as needle guide 136 and in which needle 30 moves during its oscillating motion. Holding device 124 for disk 122 is suitably fastened to head piece 14 and housing 10. The two disks are aligned with respect to each other in such fashion that their circumferential surfaces are opposite one another in the same plane. Their rotational axes lie in a common plane which is directed perpendicularly to the direction of motion of the suturing machine. Disk 122 is a free-wheeling disk which rolls on the outside surface of tissue 106 as the tissue edges are sutured together and therefore rotate.

The following is a brief description of the operation of the surgical suturing machine.

Figure 11:
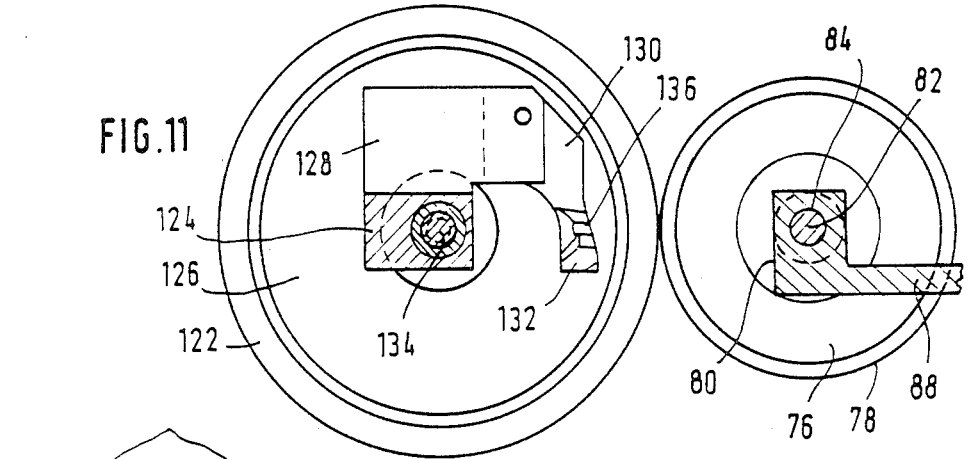
FIG. 11 is a section along line XI—XI in FIG. 10.
Figure 12:
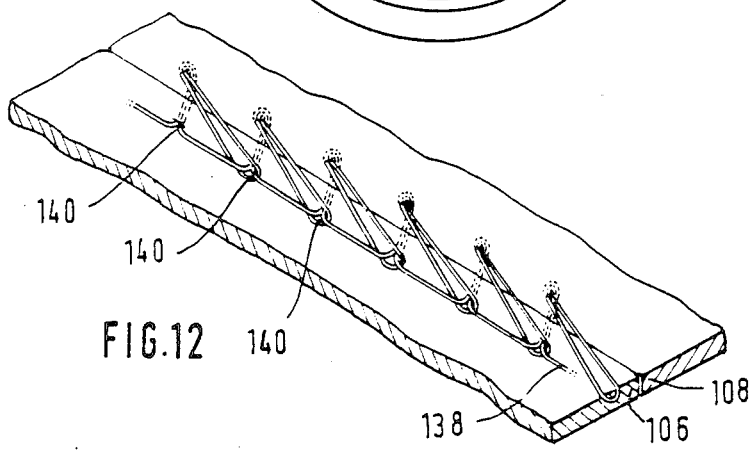
FIG. 12 is a schematic representation of the thread seam.

With the aid of lever 92 disk 76 is disengaged from the second clamping element, which is either the fixed foot with plate 70 or a rotatable disk. Tissue edges 106 and 108 to be sutured are now guided, projecting upward and abutting one another, between disk 76 and plate 70, whereupon disk 76 is moved in the direction of plate 70 with the aid of lever 92. RThe compressive force of disk 76 is determined by the spring force of coil spring 104. Now the drives to move needle 20 and thread catcher 18 are set in motion and tissue edges 106 and 108 are sutured together as the surgical suturing machine moves in the direction of arrow A in FIG. 2. At the beginning of a motion cycle the needle moves, starting at the position shown in FIG. 1, in the direction of projecting tissue edges 106 and 108, pierces the latter, and pulls suture thread 34, fed through its eye 32a, through tissue edges 106 and 108. To stabilize the motion of needle 30, as shown in FIG. 11, a needle guide 136 can be associated with clamping element 132. When needle 30 has reached its reversal point, it moves back again through tissue edges 106 and 108. Because of the friction of suture thread 34 against the tissue, the thread throws a loop. Thread catcher 18 reaches through this loop of thread formed during the backward motion of needle 30, said catcher moving in the feed direction of the surgical suturing machine during the backward motion of needle 30. When needle 30 has left the tissue edges again, thread catcher 18 has completely engaged the loop of thread. Now thread catcher 18 describes part of an arc of a circle so that it moves the loop over tissue edges 106 and 108 and guides it to the tissue edge 106 where the needle will next penetrate. During this time the surgical suturing machine advances in the direction of arrow A. In the meantime needle 30 has reached its second reversal point and is now moving back again toward tissue edges 106 and 108. Along with this motion of needle 30 thread catcher 18 moves, backward, opposite to the advance direction A of the surgical suturing machine, whereupon the thread loop laid around prongs 40 and 44 is pulled back slightly by hook 42 on prong 40. Needle 30 continues moving toward the tissue edges in the space between the two prongs 40 and 44, and hence through the loop. While needle 30 penetrates tissue edges 106 and 108 and passes through them, thread catcher 18 describes a partial arc of a circle, which brings it over tissue edges 106 and 108 to the other side of the suture, where it is in position to receive the loop of thread thrown during the next backward motion of needle 30. The projecting tissue edges 106 and 108 are pressed flat by stretcher 22 which moves on an elliptical circular path. The suture thus produced is shown in FIG. 12. As we can see, the interface between the two tissue edges 106 and 108 is spanned by thread loops. The two tissue edges 106 and 108 thus cannot move away from one another. Nozzles can be disposed on the underside of stretcher 22, through which nozzles paste or adhesive can be applied to the suture as the edges of the tissue are flat. This protects the suture against damage. The suture shown in FIG. 12 has the advantage that it can be easily removed. For example, pulling on thread end 138 permits all of the suture thread to be simply pulled out of tissue edges 106 and 108. Hence, removal of sutures is very simple in this reliable and durable suture.

A thread cutter can be disposed in the vicinity of plate 70 which, after completion of a suture, cuts off the thread loop at a point and thus creates the prerequisite for pulling the thread through the loop to knot the thread. This assumes however that the suturing machine has a motor which is fitted with a synchronizer and shuts off the suturing machine when the thread catcher 18 is centrally located above the tissue edges.

The spacing of sutures 140 in tissue edge 106 is determined by the feed or advance of the surgical suturing machine in the direction of arrow A. This advance can be accomplished manually but it is also possible for disk 76 to be driven stepwise by a stepper or freewheel. This drive can be provided for example by the motion of stretcher 22. The stepwise motion of disk 76 in the direction of arrow B in FIG. 7 advances the surgical suturing machine in the direction of arrow A. The forward motion of the surgical suturing machine is also supported by the motion of stretcher 22. The movable parts disposed on head side 14 of housing 10 of the surgical suturing machine, as for example needle holder (16), thread catcher (18), cylindrical bodies (20), stretcher (22), and the foot with the plate (70) can be mounted quickly and simply on head piece 14 by quick connections. This permits simple sterilization and rapid replacement of parts.

The second embodiment of the surgical suturing machine has a housing (200) on which a handle (not shown) is fastened. Shaft (201) is mounted on the housing, said shaft having a needle holder (202) on the end projecting from the housing. A curved needle (203) is clamped in needle holder (202) and has a suture threaded in it. In order to drive shaft (201) in an oscillating fashion, its end away from needle holder (202) has a pinion (204) mounted on it, said pinion meshing with a piston rod (205) partially made in the form of a rack. Piston rod (205) is part of a single-acting compressed air cylinder mounted on housing (200). A compression spring (207) is mounted on piston rod (205) inside compressed air cylinder (206), said spring abutting piston (208).

To form a single thread overlapping or overcast suture, a thread catcher (209) oscillating transversely to the suturing direction and moving back and forth in the suturing direction cooperates with needle (203). Thread catcher (209) is mounted on a push rod (210) which is axially displacably mounted in a bushing (211). Push rod (210) is prevented from turning by a crosspin (212) guided in a slot (213) in bushing (211).

Figure 14:
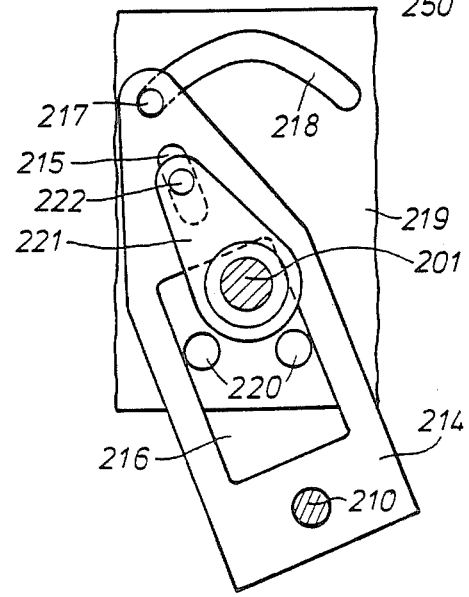
FIG. 14 is a view of a part of the drive mechanism for the thread catcher.

Bushing (211) is mounted on a swash plate (214), which as shown in FIG. 14 has an elongated hole (215) and a rectangular cutout (216) as well as a pin (217) projecting crosswise. Pin (217) is guided in an arcuate groove (218) formed in a guide plate (219) mounted on housing (200). Swash plate (214) is guided laterally by two pins (220) mounted in guide plate (219) and engaging recess (216). A drive lever (221) is mounted on shaft (201) and has a pin (222) engaging elongated hole (215).

A helical gear wheel (223) is mounted on shaft (201), said wheel meshing with helical gear wheel (224) which is mounted on a pin (225) mounted transversely to shaft (241). A pin (226) is mounted on one end of wheel (224), said pin being surrounded by a fork (227) permanently attached to pushrod (210).

An arcuate tubular section (229) is pivotably mounted on a support arm (228) mounted on housing (200), the lower end of said section being in the form of a wedge-shaped, flat, tapered suction foot (230), which has a suction opening (231) on the bottom. At the upper end of tube section (229) a hose (232) is attached, connected to a two-way valve (234) controllable by a pushrod (233). Valve (234) as shown in FIG. 16 is held in the open position by a spring (235), in which a source of suction air (260) is connected with suction foot (230). When needle (203) is pivoted backward, pushrod (233) is actuated by needle holder (202), switching valve (234) to the closed position.

Tubular section (229) is engaged by an L-shaped arm (236) which has a transversely projecting rod (237) at its upper end. Pin (237) is guided in a curved groove (238) on an arcuate guide plate (239) mounted on needle holder (202). Elements (228 to 239) form a suction air holding device (240).

A drive lever (241) is mounted on shaft (201), the upper end of said lever being forked. Drive lever (241) surrounds with its fork-shaped end a drive lever (242) projecting transversely from a known and therefore not described in greater detail) stepper (243). Stepper (243) drives a shaft (244) received in a bushing (245) mounted on housing (200). A plate-shaped transport wheel (246) is mounted on the lower end of shaft (244), said wheel having a plurality of short needles (247) on its circumferential surface.

A support (248) is pivotably mounted by a pivot pin (249) on housing (200). A likewise plate-shaped transport wheel (250) provided with needles (247) is mounted freely rotatably on the lower end of support (248). An axially movable actuating rod (252) is disposed in a extension (251) of housing (200). A transversely projecting pin (253) is disposed at the lower end of actuating rod (252), said pin engaging elongated hole (254) formed in one arm (255) of support (248). A compression spring (256) composed of an actuating rod (252), said spring abutting at one end extension (251) and at the other end a locking ring (257) disposed of an actuating rod (252), thereby urging transport wheel (250) in the direction of transport wheel (246).

Transport wheel (250) can easily be connected in a driving relationship with stepper (243) as well. For this purpose transport wheel (250) would have to be fastened to a shaft disposed in support (248), said shaft in turn being connected by a cardan joint with stepper (243).

Shaft (201) can also be driven in an oscillating fashion in another way than by compressed air cylinder (206), for example by a manually operated switching mechanism or an eccentric drive. In addition the oscillating driving motion can be generated by a drive means which is spacially separate from the suturing machine and conducted into the suturing machine by a flexible shaft.

FUNCTION

To feed the tissue edges to be connected together (261, 262) between the two transport wheels (246, 250), transport wheel (250) is swung out laterally by raising actuating rod (252). After tissue edges (261, 262) are introduced, actuating rod (252) is released, whereupon compression spring (256) moves transport wheel (250) in the direction of transport wheel (246). At this point some of needles (247) on the two transport wheels (246, 250) penetrate tissue edges (261, 262) with their points, whereupon the latter is engaged positively without being significantly injured.

Figure 13:
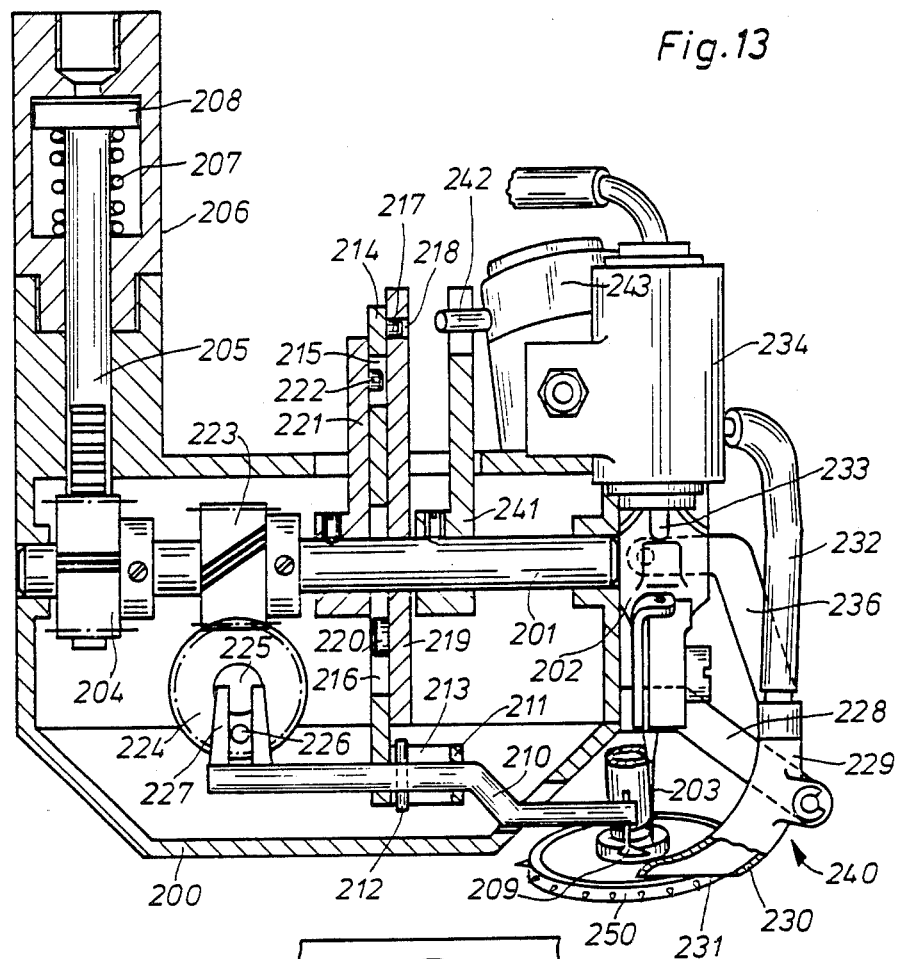
FIG. 13 is a partially cut away view of the second embodiment of the surgical suturing machine with the holding device for the tissue edges.

With the suturing machine in the resting position shown in FIGS. 13 and 15, pushrod (233) of valve (234) is actuated so that the valve is in the closed position. With valve (234) in this position the same air pressure prevails at suction opening (231) of suction foot (230) as in the environment, so that suction foot (230) does not exert a holding function.

To perform a suturing process, the suturing machine is actuated by brief pressurization with compressed air (206), whereupon piston (208) is moved downward. Piston (208) can the return to its original position from the upper position under the action of compression spring (207). As a result of this driving motion shaft (201) is moved in an oscillating fashion through an angle whose size depends on the length of the piston travel. As soon as needle holder (202) has released pushrod (233), valve (234) is switched to the open position by spring (235), whereupon a vacuum is creaed at suction opening (231) of suction (230). As a result of this vacuum, cut edges (263, 264) of tissue edges (261, 262) are sucked up by suction foot (230) and held fast.

Before needle (203) penetrates the edges of the tissue, guide plate (239), moving jointly with needle (203), because of the relative motion between curved groove (238) and pin (237), has swung arm (236) and hence suction foot (230) upward. In this fashion, suction foot (230) holds tissue edges (261, 262) at the level required for reliable suturing with respect to the path of motion of needle (203).

The holding force of suction foot (230) is so great that the forces acting on tissue edges (261, 262) during insertion of needle (203) as well as subsequent passage of the needle through the tissue and its return are taken up by suction foot (203).

During rotation of shaft (201) drive lever (221) causes swash plate (214) to tilt around pin (220), whereupon it executes a lifting motion corresponding to the shape of groove (218). As a result of this motion of swash plate (214) thread catcher (209) performs an arcuate motion which goes beyond cut edges (263, 264) and the flat part of suction foot (230). This motion has superimposed upon it a motion which is evoked by oscillating pin (226) parallel to cut edges (263, 264) so that thread catcher (209) executes a motion which is curved in three dimensions.

At the beginning of the return pivoting motion of needle (203) the suture thread forms a loop which thread catcher (209) enters. Then thread catcher (209) guides the loop over suction foot (230) to the opposite side and places it ahead of the point where needle (203) will be inserted next. Before needle (203) executes a new pivoting motion when compresed air cylinder (203) is energized once again, thereby entering the thread loop, stepper switch (203) is actuated with needle (203) in the starting position and hence with valve (234) in the closed position by means of drive lever (241), whereupon transport wheel (246) is rotated through a certain angle. As a result of this rotation of transport wheel (246) the suturing machine advances by the amount of the suture length relative to the tissue edges (261, 262). This advancing motion of the suturing machine pulls the thread loop lying above suction foot (230) off the suction foot and spreads it out to the point where needle (203) can penetrate the thread loop reliably during the next suturing process.

We claim:

1. A surgical suturing machine for connecting tissue edges having outer surfaces using suture thread, comprising: a surgical suturing machine housing; needle means carrying the suture thread, connected to said housing for reciprocating motion for passing the suture thread through the tissue edges; thread catcher means, connected to said housing for movement cooperating with said needle means to catch suture thread passed through the tissue edges by said needle means; drive means supported by said housing for driving the needle means so said needle means reciprocates between a first position and a second position and for driving the thread catcher in a generally elliptical path; first clamping element connected to said housing; and, a second clamping element having a cylindrical body connected to said housing and mounted for rotation, said first and second clamping elements each abutting outer surfaces of the tissue edges to position tissue edges in a clamping zone, the clamping zone being traversed by said needle means as it reciprocates between the first position and the second position, said second clamping element having a circumferential portion which rolls on the outer surface of one tissue edge as the housing is moved relative to the tissue edges.

2. A surgical suturing machine according to claim 1, wherein: said cylindrical body is mounted on a rotational axis shaft, said rotational axis shaft being connected to adjusting means to move said rotational axis shaft between an engaged position and a disengaged position for positioning a cylindrical body into an engaged position in which the cylindrical body cooperates with the first clamping element to position tissue edges in a clamping zone and a disengaged position in which the cylindrical body is positioned away from the clamping zone, the lower portion of the cylindrical body forming a sliding surface.

3. A surgical suturing machine according to claim 2, wherein: said adjusting means includes a spring element and a spring force adjusting element, the spring element urging said cylindrical body toward said clamping zone to provide a clamping force, the spring force adjusting element acting to vary the clamping force.

4. A surgical suturing machine according to claim 1, wherein: said cylindrical body may be lowered into a clamping zone on a feed side of the tissue edges, the cylindrical body being shaped like a drive ring.

5. A surgical suturing machine according to claim 1, further comprising: needle guide means associated with one of said first and second clamping elements for stabilizing the motion of the needle.

6. A surgical suturing machine according to claim 1, further comprising: tissue support means connected to at least one of said first and second clamping elements to support excess tissue in the vicinity of the clamping zone.

7. A surgical suturing machine according to claim 1, wherein: said cylindrical body is in the form of a circular disk.

8. A surgical suturing machine according to claim 1, further comprising: stretcher means connected to said housing for movement relative to the housing for pressing the tissue edges substantially flat after the tissue edges have passed through the clamping zone as the housing is moved relative to the tissue edges.

9. A surgical suturing machine according to claim 8, wherein: said stretcher means includes a presser foot movable in a generally elliptical path, said drive means including means for driving the stretcher means in an elliptical path.

10. A surgical suturing machine according to claim 9, wherein: said cylindrical body is driven by said presser foot as said presser foot is moved relative to said housing.

11. A surgical suturing machine according to claim 1, wherein: said thread catcher means includes a forked arm, the forked arm movable axially on a path, the path defining an arc of a circle, the forked arm being driven in synchronization with said needle means so the thread catcher means catches the suturing thread after the needle means passes through the tissue, the thread catcher means catching the thread adjacent a top of the clamping zone, and the thread catcher means placing the thread adjacent the clamping zone in front of the needle means before the next penetration of the needle means through the tissue.

12. A surgical suturing machine according to claim 1, wherein: said housing is provided with a gripper element, the housing being releasably connected to a needle holder associated with said needle means, and a thread catcher associated with said thread catcher means.

13. A surgical suturing machine according to claim 1, further comprising: a suction holding means connected to said housing for suction holding of the tissue edges adjacent the clamping zone, said suction holding means being activated as said needle means passes the suture thread through the tissue edges.

14. A surgical suturing machine according to claim 13, wherein: said suction holding means is movable up and down in a vertical plane by a suction holding drive means connected to said housing.

15. A surgical suturing machine according to claim 14, wherein: said suction holding drive means is connected with said drive means, the distance of up and down movement being adjustable.

16. A surgical suturing machine according to claim 13, wherein: said suction holding means includes a suction holding valve controllable in synchronization with the motion of said needle means to supply and cut off suction air in said suction holding means.

17. A surgical suturing machine according to claim 13, wherein: said suction holding means includes a suction foot having a planar portion, said suction foot having a suction opening on its planar portion.

* * * * *